United States Patent [19]

Isshiki et al.

[11] 4,083,869

[45] Apr. 11, 1978

[54] PROCESS FOR PRODUCING IMINE COMPOUNDS

[75] Inventors: Tomiya Isshiki; Tetsuo Tomita; Mitsuo Abe, all of Tokyo; Norio Takeda, Matsudo; Mitsuo Miura, Tokyo, all of Japan

[73] Assignee: Mitsubishi Gas Chemical Company, Inc., Tokyo, Japan

[21] Appl. No.: 831,264

[22] Filed: Sep. 7, 1977

[30] Foreign Application Priority Data

Dec. 2, 1976 Japan .................................. 51-144900

[51] Int. Cl.$^2$ ............................................ C07C 119/00
[52] U.S. Cl. ............................................... 260/566 R
[58] Field of Search ................................... 260/566 R

[56] References Cited

U.S. PATENT DOCUMENTS

| 3,636,110 | 1/1972 | Weingarten et al. | 260/566 R |
| 3,642,897 | 2/1972 | Hardtmann | 260/566 R |

OTHER PUBLICATIONS

Strain, J. Am. Chem. Soc., vol. 52, pp. 820-823 (1930), "Ammonolysis of Ketones".
Compt. rend. vol. 169, p. 239 (1915).
Arch. Pharm., vol. 243, p. 395 (1905).
Chem. Letter, vol. 1974, pp. 89, 1079.
Yuki Gosei Kagaku, 33, No. 6, pp. 454-455 (1975).

*Primary Examiner*—Gerald A. Schwartz
*Attorney, Agent, or Firm*—Armstrong, Nikaido, Marmelstein & Kubovcik

[57] ABSTRACT

An imine compound is produced in high yield by reacting a benzophenone with ammonia in the presence of 0.01 to 100% by weight of an oxide of at least one of metals selected from the group consisting of metals of the second to fifth periods of Group III to V of the periodic Table, and iron as a catalyst at a reaction temperature of 150° to 250° C on the basis of benzophenone. Ammonia is fed to the reaction system continuously under a pressure of 2 to 15 atmospheres. A solvent may be used for the reaction. The catalyst metal oxide can be readily recovered and reused without any influence of water formed by the reaction.

11 Claims, No Drawings

PROCESS FOR PRODUCING IMINE COMPOUNDS

This invention relates to a process for producing imine compounds by reaction of benzophenones with ammonia, and more particularly to a process for producing diphenylmethaneimines in a liquid phase by condensation reaction of benzophenones with ammonia.

Processes for producing diphenylmethaneimines by reaction of benzophenones with ammonia are known. For example, there are disclosed a process comprising catalytic reaction in a gaseous phase of gaseous benzophenones with ammonia over a thorium oxide catalyst at a temperature of 390° C [Compt. rend. 169 (1919), page 239], a process comprising saturating an ethanol solution of benzophenones with ammonia and heating the saturated solution at 150° to 180° C in a liquid phase [Arch. Pharm. 243 (1905) page 395], and a process comprising adding zinc chloride and ammonium chloride to molten benzophenones and reacting the benzophenones with ammonia in a liquid phase at 200° C (Chem. Lett. 1974 pages 89 and 1079). However, reaction of benzophenone with ammonia at a high temperature in a gaseous phase has such disadvantages that the raw material benzophenones undergo decomposition to by-produce nitriles, etc. Use of such salts as zinc chloride, aluminum chloride, etc. as the catalyst, or use of strong acids, as the catalyst has such problems that water formed by the reaction reacts with the catalyst to make the recovery or reuse of the catalyst difficult or that apparatus are liable to the corroded. The reaction never proceeds without the catalyst at all.

The present inventors have made extensive studies of overcoming these disadvantages and problems, and have found a novel process having none of such disadvantages and problems.

The present invention provides a process for producing an imine compound represented by the general formula:

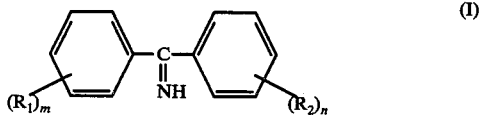
(I)

which comprises reacting a compound represented by the general formula:

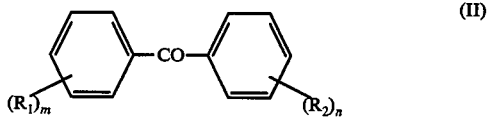
(II)

with ammonia in the presence of an oxide of at least one of metals selected from the group consisting of metals belonging to the second to fifth periods of groups III to V of the Periodic Table, and iron as a catalyst, wherein $R_1$ and $R_2$ represent hydrogen atoms, halogen atoms and alkyl, alkoxy and nitro groups, and $R_1$ and $R_2$ may be the same or different from each other, and $m$ and $n$ are integers of 1 to 5.

The oxides of metals belonging to the second to fifth periods of Groups III to V of the Periodic Table to be used as the catalyst in the present invention include, for example, oxides of metal elements of Group III such as boron, aluminum, etc., oxides of metal elements of Group IV such as silicon, titanium, zirconium, tin, etc.; and oxides of metal elements of Group V such as antimony, etc., and are selected as the catalyst for the present invention. In the present invention, an oxide of iron can be also used as the catalyst.

These metal oxides may be used not only singularly but in a combination of at least two, and can be recovered and reused without any reaction with water formed by the reaction or ammonia at a reaction temperature of 150° to 250° C.

These metal oxides can be used in any form, for example, granular form or powdery form. In the case of using granular metal oxides, a fixed bed type reactor is appropriate. In the case of the powdery metal oxides, the metal oxide powders may be dispersed in molten benzophenones and used with stirring.

The amount of the metal oxides to be used as the catalyst is not particularly limited, but generally 0.01 to 100% by weight, particularly 0.1 to 50% by weight, and more particularly 0.5 to 20% by weight of the metal oxides is preferable on the basis of the raw material benzophenone.

The reaction is carried out in a liquid phase in the present invention. The reaction temperature may be 150° to 250° C, and preferably about 200° C. The reaction pressure is not particularly limited, but an increased pressure under ammonia, is preferable to enhance the conversion. That is, 1 to 50 atmospheres, particularly 2 to 15 atmospheres, is preferable. It is preferable to continuously feed ammonia in a gaseous phase to a reaction system to make it react with the benzophenones in the presence of said catalyst. Feed rate of ammonia per one mole of the benzophenones may be 0.1 to 100 Nl/min., preferably 0.5 to 10 Nl/min.

The reaction may be carried out in the presence of a solvent in the present invention. That is, when benzophenone is used as the raw material, it is sufficiently kept in a liquid state at the reaction temperature, because its melting point is 49° C. Since its liquid viscosity is also about 1 cp, a good ammonia dispersion can be obtained. Therefore, it is not always necessary to use a solvent, but an ammonia concentration in the reaction system can be increased, depending upon the kind of the solvent, and thus the use of a suitable solvent is effective for enhancing the reaction rate. Further advantage of using the solvent is that the benzophenone can be transferred in a liquid state at room temperature.

The solvent to be used in the present invention includes alcohols such as butanol, ethyleneglycol, and glycerine, amides such as benzamide, and dimethylformamide, and aromatic compounds such as toluene, xylene, psendocumene, t-butylbenzene and o-dichlorobenzene.

The benzophenones to be used as the raw material suitable for the present invention include 2-methylbenzophenone, 3-methylbenzophenone, 4-methylbenzophenone, 4-chlorobenzophenone, 4-nitrobenzophenone, 4-methoxybenzophenone, etc. beside benzophenone.

The metal oxide catalyst of the present invention never loses its catalytic activity by the water formed by the reaction, and benzophenoneimines can be obtained in high yield while recovering and reusing the catalyst.

Now, the present invention will be explained in detail, referring to Examples, but will not be restricted to these Examples.

EXAMPLE 1

18.2 g of benzophenone and 0.240 g of powdery aluminum oxide were fed to a reactor. The resulting mixture was kept at 200° C and stirred while passing ammonia at a feed rate of 50 ml/min. under the atmospheric pressure. Excess ammonia gas passing through the liquid reaction mixture was cooled in a cooler to liquefy the formed water contained in the ammonia gas and collect it in a receiver.

The ammonia gas was passed through the reaction mixture in this manner for two hours, and then the reaction mixture was cooled, and suction filtered to separate aluminum oxide. A portion of the filtrate was taken out, diluted with benzene, and analyzed directly by gas chromatography. Benzophenoneimine was detected in yield of 31%.

EXAMPLE 2

Reaction was carried out in the same manner as in Example 1 except that 0.100 g of powdery silica.alumina (N-631L, a product of Gaschro Kogyo K.K., Japan, containing 13% $Al_2O_3$) was used. The reaction was continued for 2 hours, and benzophenoneimine was detected in yield of 45%.

EXAMPLE 3

Reaction was carried out in the same manner as in Example 1, except that 0.100 g of $H^+$-substituted molecular sieves prepared by dipping powdery molecular sieves 13X (a product of Nishio Kogyo K.K., Japan) in an aqueous 20% ammonium chloride solution for one night, and calcining the sieves at 600° C for 5 hours after filtration and water washing was used as the catalyst. The reaction was continued for two hours, and benzophenoneimine was detected in yield of 38%.

EXAMPLES 4 – 8 AND COMPARATIVE EXAMPLE

Catalytic actions of various metal oxides were investigated in the same manner as in Example 1, and the results are given in Table 1.

Table 1

| Example No. | Metallic oxide Species | Amount used (g) | Benzophenone-imine yield (%) |
|---|---|---|---|
| 4 | Titanium oxide | 0.160 | 14 |
| 5 | Iron oxide | 0.320 | 28 |
| 6 | Zirconium oxide | 0.246 | 12 |
| 7 | Tin oxide | 0.302 | 30 |
| 8 | Antimony pentoxide | 0.647 | 33 |
| Comparative Example | Thorium oxide | 0.528 | 5 |

EXAMPLES 9 – 10

Catalytic actions of various silica compounds were investigated in the same manner as in Example 2, and the results are given in Table 2.

Table 2

| Example No. | Silica compounds Species | Amount used (g) | Benzophenone-imine yield (%) |
|---|---|---|---|
| 9 | Silica . boria | 0.100 | 34 |
| 10 | Silica . zirconia | 0.100 | 26 |

EXAMPLE 11

200 g of benzophenone and 2 g of 100-mesh activated alumina (a product of Nishio Kogyo K.K., Japan) were fed to a stainless steel autoclave having an inside capacity of 500 ml with a thermowell, a gas injection inlet, a gas withdrawal outlet, and a pressure gage. Then, the autoclave was externally heated, and ammonia was continuously fed to the autoclave at a feed rate of 2.9 Nl/min. while keeping the contents of the autoclave at 200° C, and reaction was carried out under a pressure of 8 atmospheres for one hour. After the completion of reaction, the reaction solution was analyzed directly by gas chromatography whereby benzophenoneimine was detected in yield of 60%.

EXAMPLES 12 – 15

Reaction was carried out in the same manner as in Example 1, using various benzophenone derivatives as the raw materials, and the results are given in Table 3.

Table 3

| Example No. | Benzophenones Species | Amount used (g) | Amount of powdery alumina used (g) | Benzo-phenone-imine yield (%) |
|---|---|---|---|---|
| 12 | 2-Methylbenzophenone | 19.6 | 0.240 | 25 |
| 13 | 3-Methylbenzophenone | 19.6 | 0.240 | 29 |
| 14 | 4-Methoxybenzophenone | 21.2 | 0.240 | 23 |
| 15 | 4-Nitrobenzophenone | 22.7 | 0.240 | 30 |

EXAMPLE 16

91.1 g of benzophenone, 150 ml of ethylene glycol and 2 g of 100 mesh activated alumina (Nishio Kogyo K.K. Japan) were fed to the same reaction as in Example 11. Then the autoclave was externally heated, and ammonia was continuously fed to the reactor at a feed rate of 1.5 Nl/min. under 8 atm while keeping the contents at 180° C and reaction was conducted for 1 hour. After the completion of the reaction, the reaction solution was analysed by gas chromatography whereby benzophenoneimine was detected in yield of 56%.

EXAMPLE 17

91.1 g of benzophenone, 150 ml of tert-butylbenzene and 2 g of 200-mesh silica-alumina (Nikki Kagaku K.K., N-635) were fed to the same reactor as in Example 11. The reactor was heated, and ammonia gas was continuously fed to the reactor at a feed rate of 1.5 Nl/min, while keeping the contents at 170° C, and reaction was carried out under 8 atm. for one hour. The withdrawn gas was cooled and condensed tert-butylbenzene was refluxed into the reactor. After the completion of the reaction, benzophenoneimine was obtained in yield of 28%.

EXAMPLE 18

91.1 g of benzophenone, 150 ml of carbinol and 2 g of 100 mesh activated alumina were fed to the same reactor as in Example 11. Ammonia gas was continuously fed to the reactor at a feed rate of 1.5 Nl/min, while keeping the contents at 180° C, and reaction was carried out under 8 atm. for one hour. After the completion of the reaction, benzophenoneimine was detected in yield of 58%.

What is claimed is:

1. A process for producing an imine compound represented by the general formula:

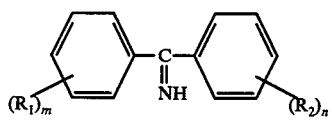

(I)

which comprises reacting a compound represented by the general formula:

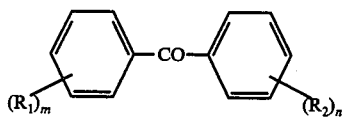

(II)

with ammonia in the presence of an oxide of at least one of the metals selected from the group consisting of metals of the second to fifth periods of Groups III to V of the Periodic Table, and iron, wherein $R_1$ and $R_2$ represent hydrogen atoms, halogen atoms, and alkyl, alkoxy and nitro groups, and $R_1$ and $R^2$ may be the same or different from each other, and $m$ and $n$ are integers of 1 to 5.

2. A process according to claim 1, wherein the reaction is carried out at 150° to 250° C.

3. A process according to claim 2, wherein the reaction is carried out at about 200° C.

4. A process according to claim 1, wherein the reaction is carried out in a liquid phase.

5. A process according to claim 1, wherein 0.01 to 100% by weight of the oxides of metal is used as the catalyst on the basis of the compound (II).

6. A process according to claim 5, wherein the oxides of metal are oxides of boron, aluminum, silicon, titanium, zirconium, tin, antimony and iron.

7. A process according to claim 1, wherein the ammonia is continuously fed to reaction system.

8. A process according to claim 1, wherein the ammonia is under a pressure of 1 to 50 atmospheres.

9. A process according to claim 1, wherein reaction is carried out in the presence of a solvent.

10. A process according to claim 9, wherein the solvent is butanol, ethyleneglycol, glycerine, benzaminodimethylformamide, toluene, xylene, pseudocumene, t-butylbenzene or o-dichlorobenzene.

11. A process according to claim 1, wherein the compound (II) is benzophenone, 2-methylbenzophenone, 3-methylbenzophenone, 4-methylbenzophenone, 4-chlorobenzophenone, 4-nitrobenzophenone, or 4-methoxybenzophenone.

* * * * *